United States Patent
Zhu et al.

(10) Patent No.: US 8,706,250 B2
(45) Date of Patent: Apr. 22, 2014

(54) NEUROSTIMULATION SYSTEM FOR IMPLEMENTING MODEL-BASED ESTIMATE OF NEUROSTIMULATION EFFECTS

(75) Inventors: Changfang Zhu, Valencia, CA (US); Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 304 days.

(21) Appl. No.: 13/244,388

(22) Filed: Sep. 24, 2011

(65) Prior Publication Data

US 2012/0165900 A1    Jun. 28, 2012

Related U.S. Application Data

(60) Provisional application No. 61/427,059, filed on Dec. 23, 2010.

(51) Int. Cl.
*A61N 1/372*  (2006.01)

(52) U.S. Cl.
USPC .................................. 607/59; 607/2

(58) Field of Classification Search
USPC .......................................................... 607/59
See application file for complete search history.

(56) References Cited

U.S. PATENT DOCUMENTS

| | | | |
|---|---|---|---|
| 6,487,451 B1 | 11/2002 | Casset et al. | |
| 6,516,227 B1 | 2/2003 | Meadows et al. | |
| 6,731,986 B2 | 5/2004 | Mann | |
| 6,895,280 B2 | 5/2005 | Meadows et al. | |
| 6,993,384 B2 | 1/2006 | Bradley et al. | |
| 2010/0010566 A1 | 1/2010 | Thacker et al. | |
| 2010/0121409 A1 | 5/2010 | Kothandaraman et al. | |
| 2012/0046715 A1 | 2/2012 | Moffitt et al. | |
| 2012/0109257 A1 | 5/2012 | Yoo et al. | |
| 2012/0165898 A1 | 6/2012 | Moffitt | |
| 2012/0165901 A1 | 6/2012 | Zhu et al. | |

OTHER PUBLICATIONS

Warman, Eduardo N., et al., Modeling the Effects of Electric Fields on Nerve Fibers: Determination of Excitation Thresholds, IEEE Transactions on Biomedical Engineering, vol. 39, No. 12, Dec. 1992.
Frankemolle, Anneke M.M., et al., Reversing cognitive-motor impairments in Parkinson's disease patients using a computational modelling approach to deep brain stimulation programming, Brain 2010, 133, 746-761.
U.S. Appl. No. 61/374,879, Entitled: User Interface for Segmented Neurostimulation Leads, Inventor: Michael A. Moffitt, et al., filed Aug. 18, 2010.

(Continued)

*Primary Examiner* — Carl H Layno
*Assistant Examiner* — Jennifer Ghand
(74) *Attorney, Agent, or Firm* — Vista IP Law Group LLP (57) ABSTRACT

A neurostimulation system for use in providing therapy to a patient comprises a user input device configured for receiving input from a user, and processing circuitry configured for selecting an electrode configuration in response to receiving the input from the user, providing an electrical model of a neuronal element of the patient, providing a discrete approximation of a differential equation of a neural response parameter (e.g., a transmembrane voltage potential) of the electrical model as a function of discrete space (e.g., nodes along the electrical model) and as a function of a finite time difference, computing the neural response parameter in the differential equation approximation at a specified time for each of a plurality of points on a membrane of the neuronal element, and performing a human-discernible function based on the computed neural response parameters.

15 Claims, 8 Drawing Sheets

(56) References Cited

OTHER PUBLICATIONS

U.S. Appl. No. 61/407,689, Entitled: System and Method for Providing Fluid Real-Time Visualization of Region of Tissue Activation, Inventor: Peter Jun Yoo, et al., filed Oct. 28, 2010.

U.S. Appl. No. 61/427,027, Entitled: Neurostimulation System for Estimating Desired Stimulation Amplitude for Electrode Configuration, Inventor: Changfang Zhu, et al., filed Dec. 23, 2010.

U.S. Appl. No. 61/427,441, Entitled: Neurostimulation System for Selectively Estimating Volume of Activation and Providing Therapy, Inventor: Michael A. Moffitt, filed Dec. 27, 2010.

NEUROSTIMULATION SYSTEM FOR IMPLEMENTING MODEL-BASED ESTIMATE OF NEUROSTIMULATION EFFECTS

RELATED APPLICATION DATA

The present application claims the benefit under 35 U.S.C. §119 to U.S. provisional patent application Ser. No. 61/427,059, filed Dec. 23, 2010. The foregoing application is hereby incorporated by reference into the present application in its entirety.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers appropriate stimulation energy to the volume of tissue that is targeted for therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, a patient care professional (e.g., a clinician, field engineer, sales representative, etc.) generally programs the neurostimulator through a computerized programming system. This programming system can be a self-contained hardware/software system, or can be defined predominantly by software running on a standard personal computer (PC), personal data assistant (PDA), or other computerized device. The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

Thus, in the application of electrical neurostimulation therapy, the goal is to identify a pertinent paradigm of stimulation that properly stimulates neural tissue. Significantly, it may sometimes be desirable to estimate or predict the stimulation effects of electrical energy applied, or to be applied, to neural tissue adjacent to electrodes based on an estimation of the membrane response (e.g. transmembrane voltage potentials) of one or more neurons induced by the actually applied or potentially applied electrical energy. For example, given a specific set of stimulation parameters, it may be desired to predict a region of stimulation within the neural tissue of a patient based on an estimation of the neuronal response. As another example, when transitioning between electrode configurations, it may be desirable to adjust the intensity of the electrical stimulation energy based on an estimation of the transmembrane voltage potentials.

Estimating the transmembrane voltage potential of a neuron in response to an applied electric field generally includes two steps: (1) computing the extracellular electric field in response to the conveyance of electrical energy from a specific electrode configuration; and (2) computing the transmembrane voltage potential of the neuron in response to the generated electric field. The calculation of the extracellular electric field is straightforward and can be done analytically or numerically. Calculating the transmembrane voltage potential, however, is more dynamic and highly non-linear in both time and space. Several neural models are now available for estimating the induced neural response to an extracellular electric field, which range from simplified analytical approximations to computationally intensive network models. In commercial neurostimulator development, the trade off between the model efficiency and computational efficiency has to always be considered.

In one computationally efficient method, a linear cable model (passive model in that the membrane conductance is constant) assumes that neuronal activation occurs if the induced depolarization is greater than a critical transmembrane voltage potential, which is commonly assumed to be fixed when, in fact, it is a function of pulsewidth. Thus, passive neural models have been considered accurate only for long pulses (steady-state polarization). In another computationally efficient method, an activating function ($2^{nd}$ spatial derivative of the external electrical field), which describes the sources that are driving the neuron, is used to estimate the membrane response of a neuron to an externally applied electric field. The activating function, however, does not include any information about the neuron, and thus provides an accurate description of the sources, but not the neural response to the sources.

Thus, neither of these methods can be used to accurately predict the neural response to an externally applied electric field. Another method has been proposed that combines the use of passive neural models and activating functions. In particular, as described in E. N. Warman, W. M. Grill, and D. Durand, *Modeling the Effects of Electric Fields on Nerve Fibers: Determination of Excitation Threshold*, IEEE Trans. On Biomed Engr. Vol. 39, No. 12, 1992, a total equivalent driving function has been proposed for estimating the transmembrane voltage potentials induced in passive cable models of neuronal elements to an externally applied electric field. This method takes into account the activating function, pulse width of the electrical stimulation energy, and passive properties of neuron models, thereby eliminating errors associated with the use of the activating function alone. However, due largely to the computational complexity involved in solving for partial differential equations to obtain the passive step response of the neuron to an intracellular electrical current stimulation, the application of a total equivalent driving function to estimate a neural response to an external applied electric field is presently limited.

There, thus, remains a need for a computationally efficient technique for estimating the stimulation effect (e.g., transmembrane voltage potential of a neuron) in the presence of an externally conveyed electric field.

SUMMARY OF THE INVENTION

In accordance with the present inventions, a neurostimulation system for use in providing therapy to a patient is provided. The system comprises a user input device configured for receiving input from a user, and processing circuitry configured for selecting an electrode configuration in response to receiving the input from the user. In one embodiment, the neurostimulation system comprises a housing containing the user input device and processing circuitry. The neurostimulation system may further comprise an external control device that includes the housing, input device, and processing circuitry.

The processing circuitry is further configured for providing an electrical model of a neuronal element of the patient, providing a discrete approximation of a differential equation of a neural response parameter (e.g., a transmembrane voltage potential) of the electrical model as a function of discrete space (e.g., nodes along the electrical model of nerve fibers) and as a function of a finite time difference (e.g., a forward time difference, a backward time difference, or a central time difference), and computing the neural response parameter of the differential equation approximation at a specified time for each of a plurality of points on a membrane of the neuronal element.

In one embodiment, the neuronal element is a neural axon, and the electrical model may be an electrical cable model of the neural axon, in which case, the processing circuitry may further be configured for estimating extracellular field potentials, induced by pulsed electrical energy theoretically conveyed by the electrode configuration, at the nodes along the electrical cable model. The processing circuitry may be configured for selecting a pulse width of the electrical energy in response to the input from the user, and computing the neural response parameters at the end of the pulse width, assuming a unit electrical energy is applied intracellularly. The processing circuitry may further be configured for computing a total equivalent driving function of the extracellular field potentials at least one of the nodes. Each of the total equivalent driving functions comprises a plurality of activating functions that are respectively weighted using the computed neural response parameters, which may have been computed based on the differential equation approximation having a unit intracellular step current.

In one embodiment, the human-discernible function is instructing a neurostimulation device to deliver electrical energy to the patient at a specified amplitude. In this case, the neurostimulation system may further comprise output circuitry via which the processing circuitry instructs the neurostimulation device to deliver the electrical energy. In another embodiment, the human-discernible function is instructing a monitor to display a region or volume of tissue activation.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
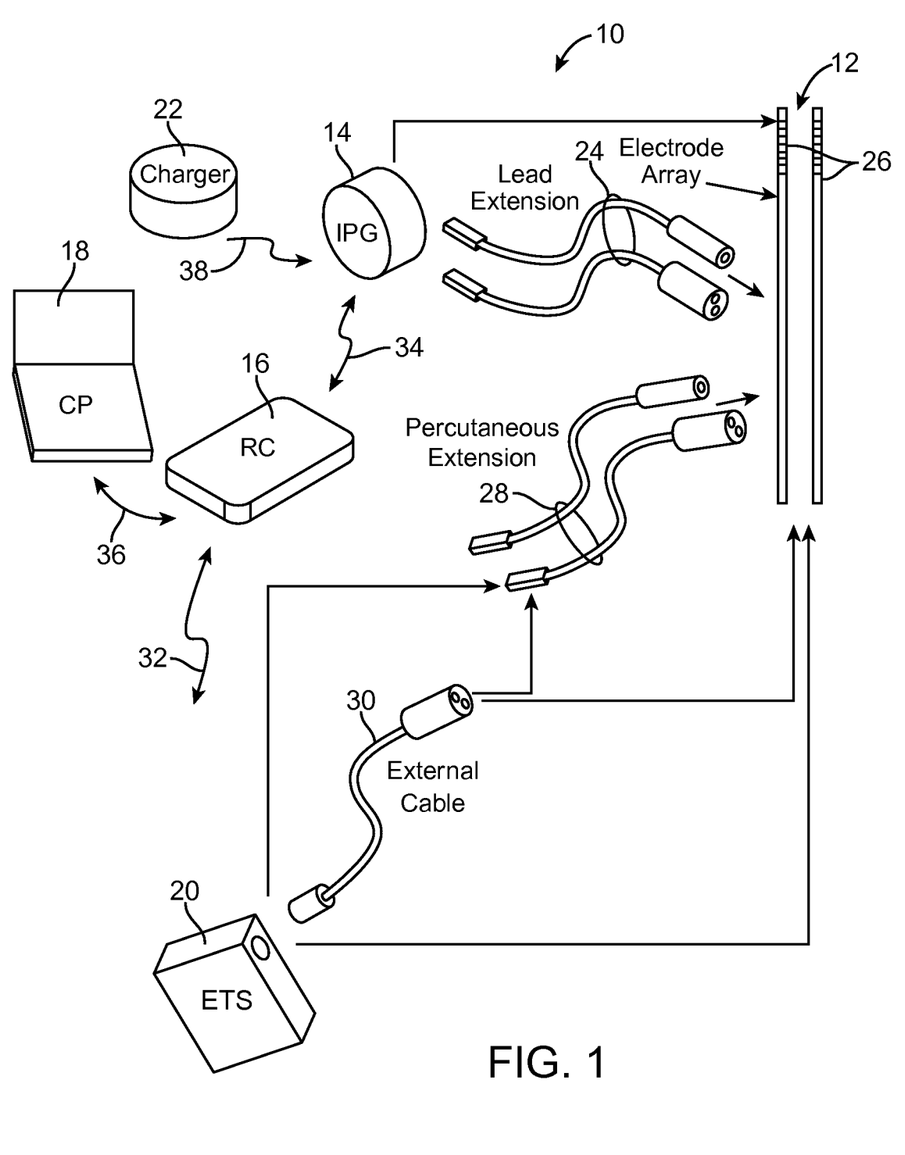
FIG. 1 is a plan view of a Spinal cord Stimulation (SCS) system constructed in accordance with one embodiment of the present inventions.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a standalone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
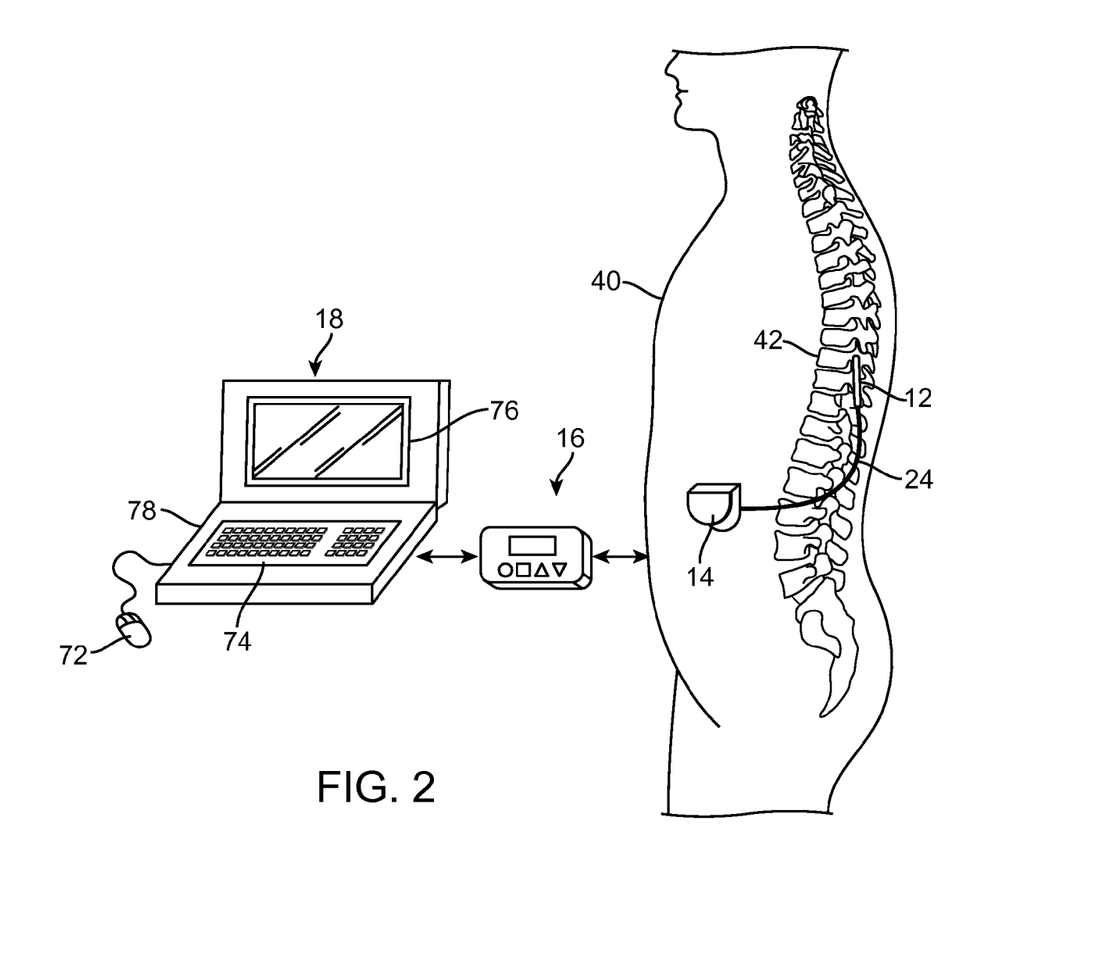
FIG. 2 is a perspective view of the arrangement of the SCS system of FIG. 1 with respect to a patient.

As shown in FIG. 2, the electrode leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
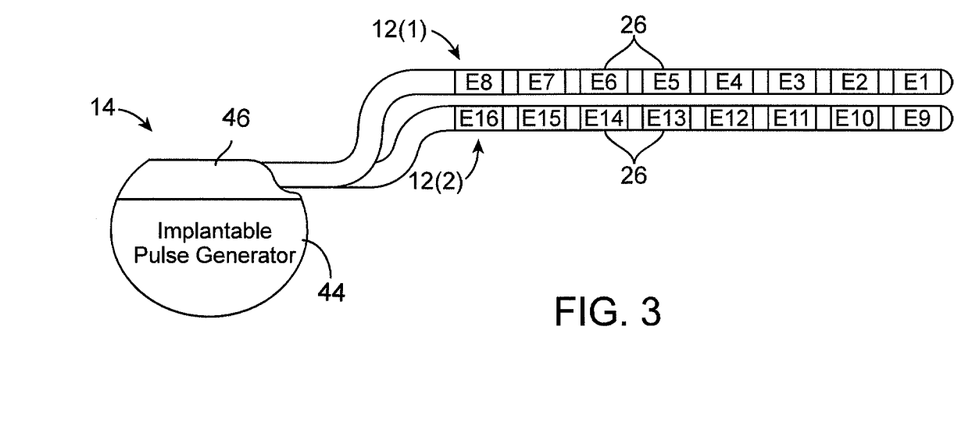
FIG. 3 is a profile view of an implantable pulse generator (IPG) and percutaneous leads used in the SCS system of FIG. 1.

Referring now to FIG. 3, the external features of the neurostimulation leads 12 and the IPG 14 will be briefly described. One of the neurostimulation leads 12(1) has eight electrodes 26 (labeled E1-E8), and the other neurostimulation lead 12(2) has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neurostimulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode combinations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
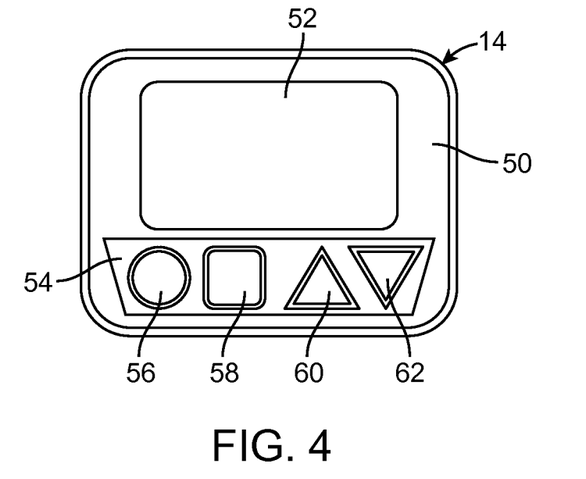
FIG. 4 is front view of a remote control (RC) used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
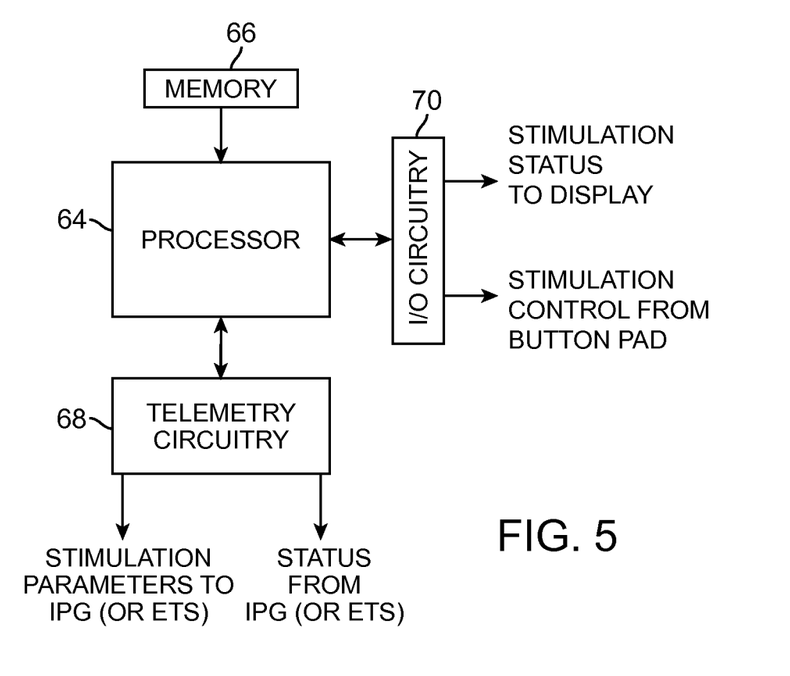
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

Figure 6:
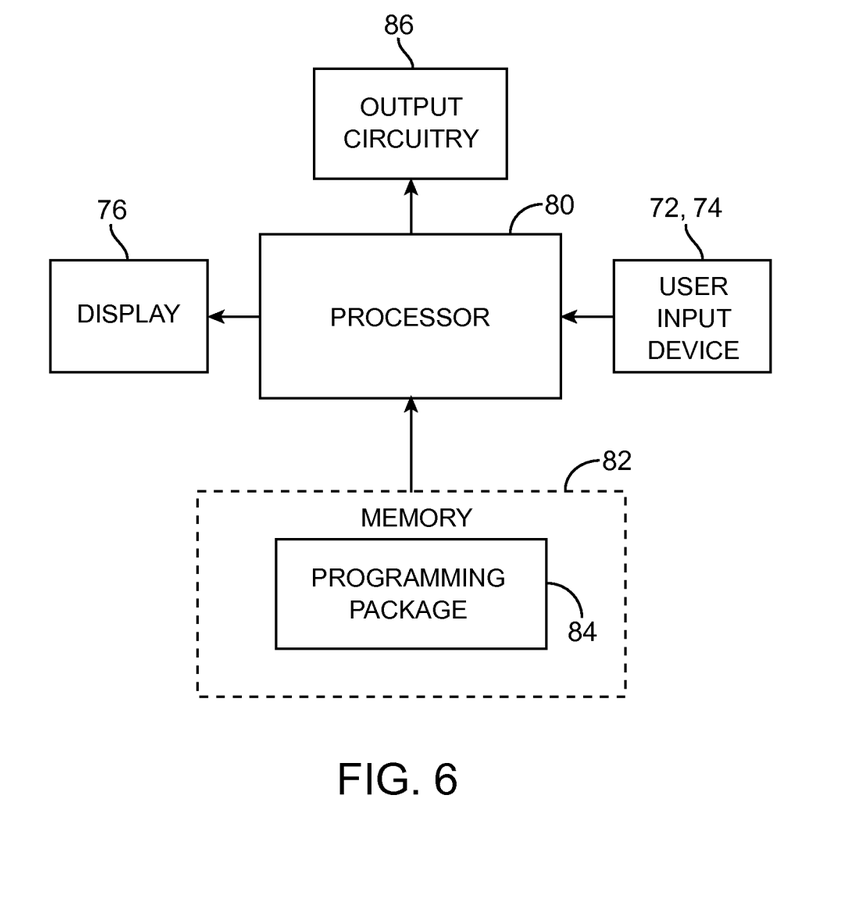
FIG. 6 is a block diagram of the internal components of a clinician's programmer (CP) used in the SCS system of FIG. 1.

Referring further to FIG. 6, to allow the user to perform these functions, the CP 18 includes a mouse 72, a keyboard 74, and a display monitor 76 housed in a housing 78. It is to be understood that in addition to, or in lieu of, the mouse 72, other directional programming devices may be used, such as a joystick, a button pad, a group of keyboard arrow keys, a roller ball tracking device, and horizontal and vertical rocker-type arm switches. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 further includes a processor 80 (e.g., a central processor unit (CPU)) and memory 82 that stores a stimulation programming package 84, which can be executed by the processor 80 to allow the user to program the IPG 14, and RC 16. The CP 18 further includes output circuitry 86 for downloading stimulation parameters to the IPG 14 and RC 16 and for uploading stimulation parameters already stored in the memory 66 of the RC 16, via the telemetry circuitry 68 of the RC 16.

Execution of the programming package 84 by the processor 80 provides a multitude of display screens (not shown) that can be navigated through via use of the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a therapeutic map (e.g., body regions targeted for therapy, body regions for minimization of side effects, along with metrics of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a more computationally efficiency technique for accurately estimating the neural response in the presence of an externally conveyed electric field, thereby providing a means for the user interface to perform human-discernible functions, such as automatically managing the stimulation amplitude of the electrical stimulation energy as electrode configurations are manually or automatically transitioned, as discussed in U.S. application Ser. No. 13/335,924, entitled "Neurostimulation System for Estimating Desired Stimulation Amplitude for Electrode Configuration," which is expressly incorporated herein by reference, or estimating and displaying a volume of tissue activation given a set of stimulation parameters, as discussed in U.S. patent application Ser. No. 13/336,580, entitled "Neurostimulation System for Selectively Estimating Volume of Activation and Providing Therapy," and U.S. application Ser. No. 13/244,415, entitled "System and Method for Providing Fluid Real-Time Visualization of Region of Tissue Activation," which are all expressly incorporated herein by reference.

Figure 7:
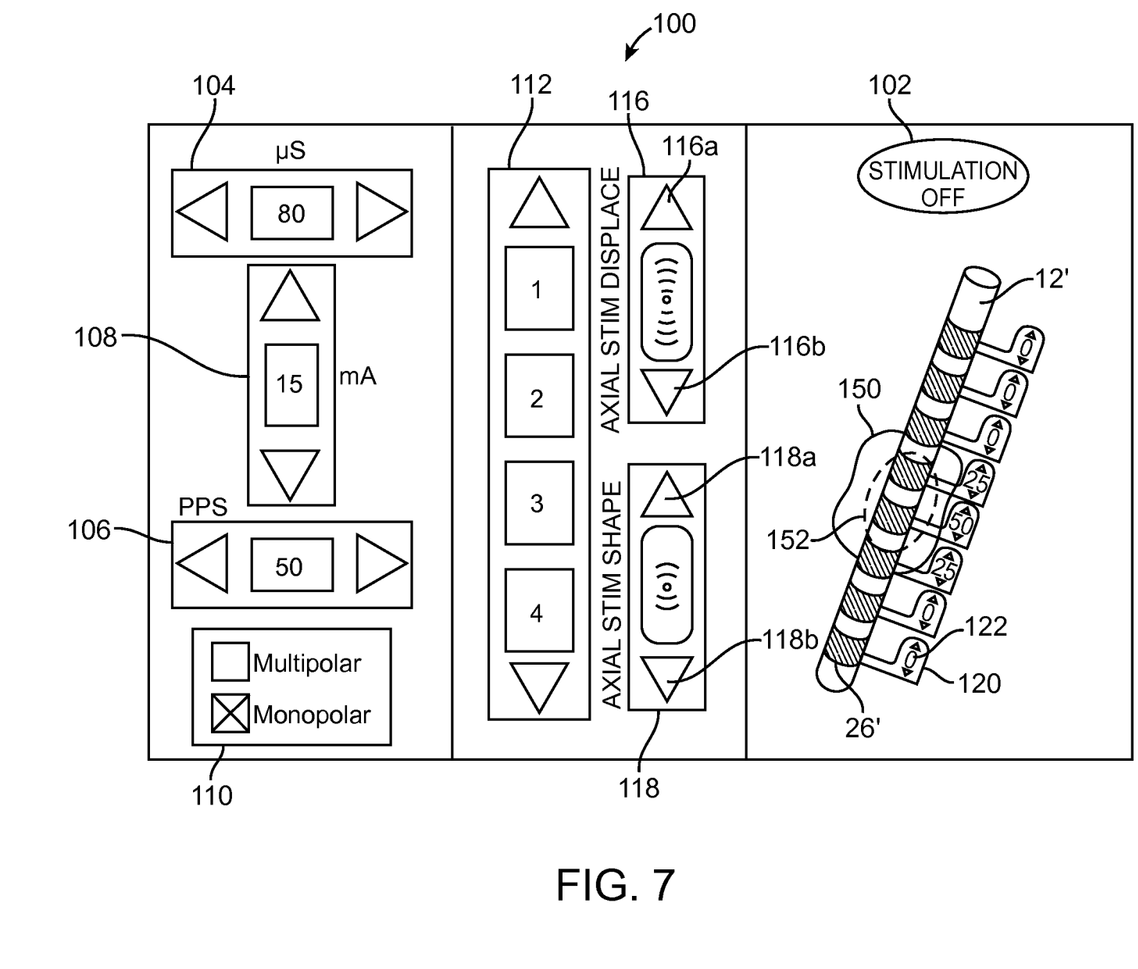
FIG. 7 is a plan view of a user interface of the CP of FIG. 6 for programming the IPG of FIG. 3.

In particular, a programming screen 100 can be generated by the CP 16, as shown in FIG. 7. The programming screen 100 allows a user to perform stimulation parameter testing. To this end, the programming screen 100 comprises a stimulation on/off control 102 that can be alternately clicked to turn the stimulation on or off. The programming screen 100 further includes various stimulation parameter controls that can be operated by the user to manually adjust stimulation parameters. In particular, the programming screen 100 includes a pulse width adjustment control 104 (expressed in microseconds (µs)), a pulse rate adjustment control 106 (expressed in pulses per second (pps), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 44 of the IPG 14 may be treated as one of the lead electrodes 26, such that both the case electrode 40 and at least one of the lead electrodes 26 can be used to convey anodic electrical current at the same time. Additionally, the case electrode may be configured with all the programmability of a lead electrode, with full anodic and cathodic fractionalization.

The programming screen 100 also includes an electrode combination control 112 having arrows that can be clicked by the user to select one of four different electrode combinations 1-4. Each of the electrode combinations 1-4 can be created using a variety of control elements.

The programming screen 100 also includes a set of axial electrical stimulation field displacement control elements 116 and a set of axial electrical stimulation field shaping control elements 118. In the illustrated embodiments, the control elements 116, 118, as well as the other control elements discussed herein, are implemented as a graphical icon that can be clicked with a mouse or touched with a finger in the case of a touchscreen. Alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements.

When any of the axial electrical stimulation field displacement control elements 116 is actuated, control signals are generated in response to which the processor 80 is configured for generating stimulation parameter sets designed to axially displace the locus of the electrical stimulation field relative to the axis of the lead 12. Preferably, the control signals that are generated in response to the actuation of the control elements 116 or the alternative control elements are directional, meaning that the locus of the electrical stimulation field will be displaced in a defined direction in response to a continual actuation of a single control element irrespective of the current position of the locus electrical stimulation field locus. When any of the axial electrical stimulation field shaping control elements 118 is actuated, control signals are generated in response to which the processor 80 is configured for generating stimulation parameter sets designed to axially expand or contract the electrical stimulation field relative to its locus.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the processor 80 is configured for generating the plurality of stimulation parameter sets. The output telemetry circuitry 86 is configured for transmitting these stimulation parameters sets to the IPG 14.

Each of the sets of control elements 116, 118 takes the form of a double arrow (i.e., two oppositely pointing control element arrows) that can be actuated to modify the electrical stimulation field depending on the mode of operation. For example, an upper arrow control element 116*a* can be clicked to axially displace the locus of the electrical stimulation field (i.e., along the axis of the lead 12) in the proximal direction; a lower arrow control element 116*b* can be clicked to axially displace the locus of the electrical stimulation field (i.e., along the axis of the lead 12) in the distal direction; a lower arrow control element 118*a* can be clicked to axially contract the electrical stimulation field about its locus, and an upper arrow control element 118*b* can be clicked to axially expand the electrical stimulation field about its locus.

The locus of the electrical stimulation field may be displaced, e.g., by gradually "steering" or shifting electrical current between electrodes in a single timing channel. For example, the locus of the electrical stimulation field can be gradually displaced axially in the distal direction along the lead 12 by gradually including electrodes in a stimulating electrode group and gradually excluding other electrodes from the stimulating electrode group in the single timing channel.

The locus of the electrical stimulation field may alternatively be displaced using multiple timing channels. In particular, the electrical energy can be conveyed between different combinations of electrodes in accordance with multiple timing channels; that is, a first stimulating electrode group can be used during a first timing channel, a second stimulating electrode group can be used during a second timing channel, and so forth, and the groups may or may not overlap. The magnitude of the electrical energy conveyed in accordance with at least one of the multiple timing channels can be modified to effectively displace the locus of the stimulation region as experienced by the patient.

The electrical stimulation field can be expanded and contracted by gradually "steering" or shifting electrical current between electrodes in a similar manner described above with respect to the displacement of the locus of the electrical stimulation field, with the exception that the electrical stimulation field is expanded or contracted.

For example, the electrical stimulation field can be gradually expanded axially along the lead 12 by gradually including electrodes in a stimulating electrode group, and can be gradually contracted axially along the lead 12 by gradually excluding electrodes in a stimulating electrode group. The electrical stimulation field can be alternatively expanded and contracted using multiple timing channels in a similar manner described above with respect to the displacement of the locus of the electrical stimulation field, with the exception that the electrical stimulation field is expanded or contracted. For example, the magnitude of the electrical energy conveyed in accordance with at least one of the multiple timing channels can be modified to effectively expand or contract the stimulation field.

Further details discussing different techniques for modifying an electrical stimulation field is disclosed in U.S. Provisional Patent Application 61/374,879, entitled "User Interface for Segmented Neurostimulation Leads," which is expressly incorporated herein by reference. In an optional embodiment, additional control elements can be provided to circumferentially displace the locus of the electrical stimulation field, circumferentially contract or expand the electrical stimulation field, radially displace the locus of the electrical field, or radially contract or expand the electrical stimulation field, as disclosed in U.S. Provisional Patent Application 61/374,879.

Although the programming screen 100 illustrates only one neurostimulation lead 12 with electrodes arranged in only one dimension, thereby allowing the electrical current to only be steered in one dimension, it should be appreciated that the programming screen 100 may additionally illustrate the other neurostimulation lead 12, thereby arranging the electrodes in two dimensions and allowing the electrical current to be steered in two dimensions. In this case, using appropriate control elements (e.g., left and right arrows), the locus of the electrical stimulation field can be displaced in the transverse direction (perpendicular to the axial direction, and in this case, left or right) and/or the electrical stimulation field can be expanded or contracted in the transverse direction. Of course, the electrodes can be arranged in three-dimensions (e.g., by arranging three neurostimulation leads in three-dimensions or by using electrodes on a single neurostimulation lead that are arranged in three-dimensions, e.g., the segmented neurostimulation leads described in U.S. Provisional Patent Application Ser. No. 61/374,879), in which case, the electrical current can be steering in three-dimensions.

The programming screen 100 displays three-dimensional graphical renderings of the lead 12' and electrodes 26'. In an optional embodiment, iconic control elements 120 are graphically linked to the three-dimensional electrode renderings 26'. Continual actuation of the control elements 120 generates control signals that prompt the processor 80 to generate stimulation parameters designed to modify the electrical stimulation field, which stimulation parameters are then transmitted from the output circuitry 86 of the CP 18 to the IPG 14. In the illustrated embodiment, each of the control elements 120 has an up arrow and a down arrow that can be respectively actuated (e.g., by clicking) to respectively increase or decrease the electrical current flowing through the electrode 26 corresponding to the graphical electrode rendering 26' to which the actuated control element 120 is graphically linked.

Actuation of any of the control elements 120 essentially steers electrical current from other active electrodes to the electrode associated with the actuated control element 120 or from the electrode associated with the actuated control element 120 to other active electrodes. In this manner, the locus of the electrical stimulation field can be displaced, the shape of the electrical stimulation field can be modified, and if two separate electrical stimulation fields current exist, electrical current can be shifted from one of the electrical stimulation fields (effectively decreasing its size) to another of the electrical stimulation fields (effectively increasing its size).

The control element 120 also includes an indicator 122 that provides an indication of the amount of electrical current flowing through each of the electrodes 26 in terms of a fractionalized current value. The indicators 122 may perform this function when the respective control elements 120 are actuated or when the axial electrical stimulation field displacement control elements 116 and axial electrical stimulation field shaping control elements 118 are actuated. The programming screen 100 displays the three-dimensional graphical renderings of the lead 12' and electrodes 26' relative to a graphical representation of the anatomical structure 150 that is preferably the stimulation target. The processor 80 computes an estimate of a resulting volume of activation (VOA) 152, and generates display signals that prompt the monitor 76 to display a graphical representation of the VOA 152 with the graphical lead 12' and graphical anatomical structure 150. In the preferred embodiment, the graphical VOA 152 is superimposed over the graphical anatomical structure 150. Further details discussing technique for computing the estimate of a VOA are disclosed in A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16), which is expressly incorporated herein by reference.

As briefly discussed above, the processor 80 is configured for estimating the neural response of neuronal elements in the presence of an externally conveyed electric field. The processor 80 accomplishes this by using a finite-difference method to numerically solve a cable model involving partial differential equations for neural response parameters in a computationally efficient manner, and then using these neural response parameters to more accurately determine a total equivalent driving function. As such, estimating a neural response to electrical stimulation energy becomes amendable for implementation in real-time applications and embedded systems. Although, in the illustrated embodiment, the neural response parameters are transmembrane potentials, other parameters, such as transmembrane conductivity or transmembrane current, which can be derived as a function of the transmembrane potentials, can be used.

Figure 8:
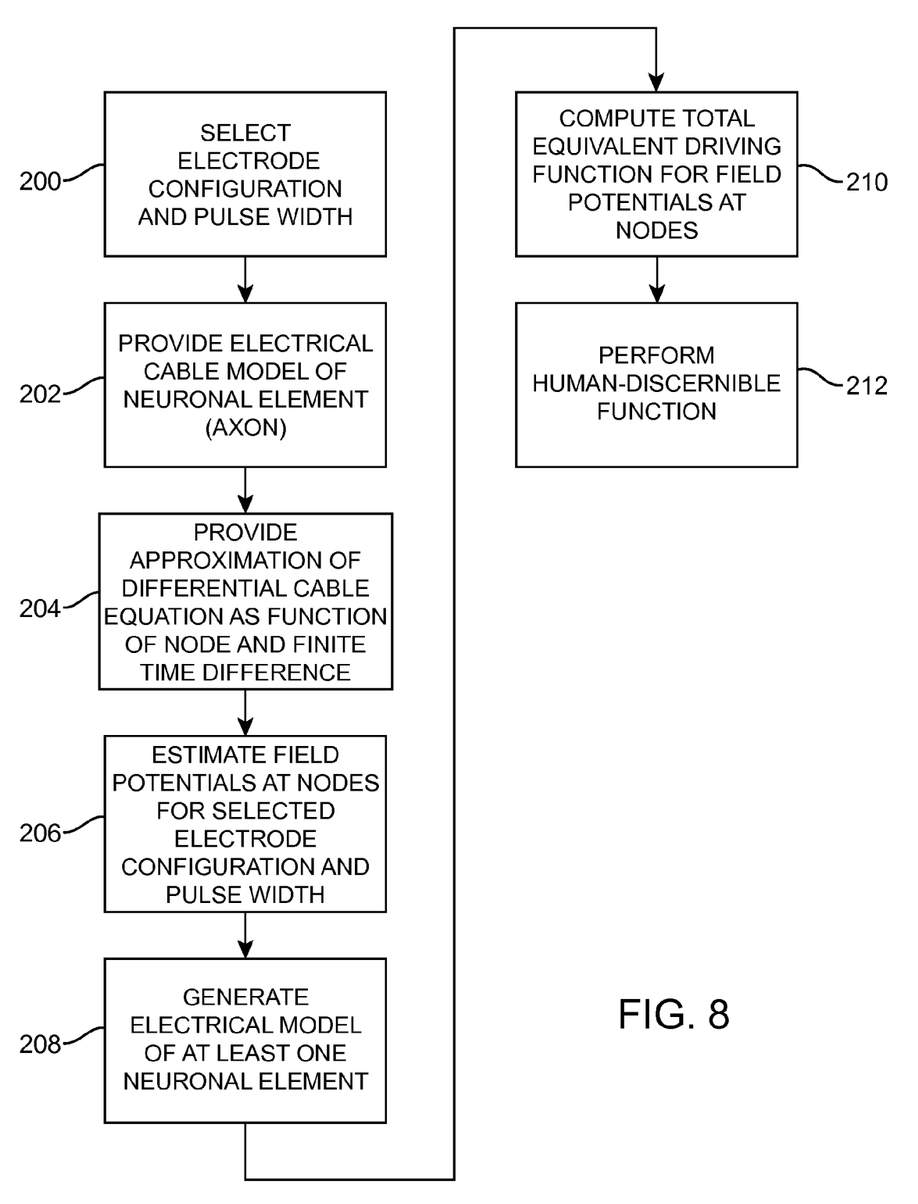
FIG. 8 is a flow diagram illustrating one method of estimating transmembrane potentials of a neuronal element.
Figure 9:
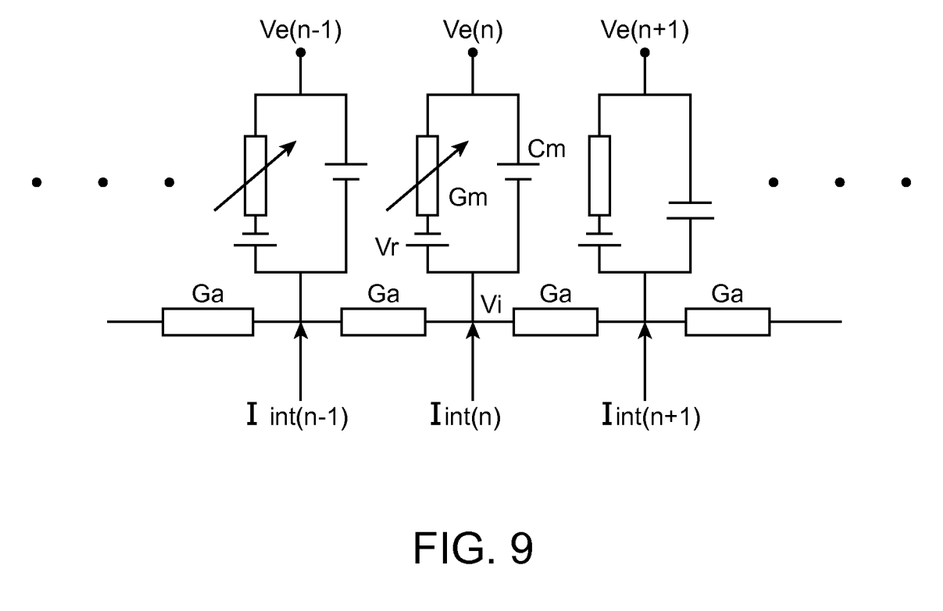
FIG. 9 is a schematic diagram of an electrical cable model taking the form of an electrical network representation of a myelinated axon.

In particular, and with reference to FIG. 8, the processor 80 selects an electrode configuration (which may be an arbitrary electrode configuration or may be selected from a predefined plurality of electrode configurations) and a pulse width in response to receiving input from the user via the programming screen 100, as described above (step 200). Then, the processor 80 provides an electrical cable model of a neuronal element (and in particular, a neural axon) of the patient (step 202). As shown in FIG. 9, the electrical cable model takes the form of an electrical network representation of a myelinated axon in an isopotential medium having time varying intracellular currents ($I_{in}(n, t)$) that are injected at a plurality of nodes (n) that are equivalent to extracellular field potentials ($V_e(n)$) induced by the electrical energy conveyed from a given electrode configuration. Three nodes of the electrical cable model, and thus, three corresponding intracellular currents ($I_{in}(n_0-1)$, $I_{in}(n_0)$, $I_{in}(n_0+1)$) and three corresponding extracellular field potentials ($V_e(n_0-1)$, $V_e(n_0)$, $V_e(n_0+1)$), are shown in FIG. 9. Also shown are the resting voltage potential $V_r$, the intracellular voltage potential $V_1$, the nodal capacitance $C_m$, the nodal conductance $G_m$, and the axoplasmic conductance $G_a$.

Applying Kirchhoff's current law to the electrical cable model of FIG. 9 in response to a unit intracellular step current $I_{in}$ yields the following differential equation:

$$C_m \frac{\partial V_m(n, t)}{\partial t} + G_m V_m(n, t) - \quad [1]$$
$$G_a[V_m(n-1, t) - 2V_m(n, t) + V_m(n+1, t)] = I_{in}(n, t),$$

where $$I_{in}(n, t) = \begin{cases} 1, & n = n_0 \\ 0, & n \neq n_0, \end{cases}$$

$V_m(n,t)$ is the transmembrane potential at node n with respect to the resting potential $V_r$. This cable equation involves partial differential equations, the solution of which describes space-time evolution of the transmembrane voltage potentials during stimulation. The finite difference method solves equation [1] by computing the variable parameters at a finite time difference $\Delta t$ and at a discrete value of space n; that is, the processor 80 provides a discrete approximation of equation [1] as a function of discrete space (and in the case, nodes n along the cable model) and as a function of a finite time difference $\Delta t$ (step 204). As such, equation [1] can be written as:

$$C_m \frac{V_m(n, t) - V_m(n, t - \Delta t)}{\Delta t} + G_m V_m(n, t) - \quad [2]$$
$$G_a[V_m(n-1, t) - 2V_m(n, t) + V_m(n+1, t)] = I_{in}(n, t),$$

which yields:

$$\left[1 + \frac{\Delta t G_m}{C_m} + \frac{2\Delta t G_a}{C_m}\right] V_m(n, t) - \frac{\Delta t G_a}{C_m} V_m(n-1, t) - \quad [3]$$
$$\frac{\Delta t G_a}{C_m} V_m(n+1, t) = V_m(n, t - \Delta t) + \frac{\Delta t}{C_m} I_{in}(n, t)$$

Several methods can be used to approximate equation [1], e.g., forward difference, backward difference, or central difference (or Crank-Nicolson) methods. In this embodiment, the backward difference method is employed, thereby resulting in the time difference factor (t−$\Delta t$). Alternatively employing the forward difference method results in the time difference factor (t+$\Delta t$), and employing the central difference method results in the time difference factor (2t−$\Delta t$+$\Delta t$)/2.

To find the solution of $V_m$ for a plurality of points on a membrane of the neuronal element (and in particular, all nodes n and time t, a matrix operation needs to be performed. Observing a boundary condition that no current flows from the fiber ends, the matrix takes the form below:

$$\begin{bmatrix} 1+\frac{\Delta t}{C_m}(G_m+G_a) & -\frac{\Delta tG_a}{C_m} & 0 & \ldots & 0 & 0 & 0 \\ -\frac{\Delta tG_a}{C_m} & 1+\frac{\Delta t}{C_m}(G_m+2G_a) & -\frac{\Delta tG_a}{C_m} & \ldots & 0 & 0 & 0 \\ 0 & \frac{\Delta tG_a}{C_m} & 1+\frac{\Delta t}{C_m}(G_m+2G_a) & \ldots & 0 & 0 & 0 \\ \vdots & \vdots & \vdots & & \vdots & \vdots & \vdots \\ 0 & 0 & 0 & \ldots & 1+\frac{\Delta t}{C_m}(G_m+G_a) & -\frac{\Delta tG_a}{C_m} & 0 \\ 0 & 0 & 0 & \ldots & -\frac{\Delta tG_a}{C_m} & 1+\frac{\Delta t}{C_m}(G_m+2G_a) & -\frac{\Delta tG_a}{C_m} \\ 0 & 0 & 0 & \ldots & 0 & -\frac{\Delta tG_a}{C_m} & 1+\frac{\Delta t}{C_m}(G_m+2G_a) \end{bmatrix}$$ [4]

$$\begin{bmatrix} V_m(1,t) \\ \vdots \\ V_m(n_0-1,t) \\ V_m(n_0,t) \\ V_m(n_0+1,t) \\ \vdots \\ V_m(N,t) \end{bmatrix} = \begin{bmatrix} V_m(1,t-\Delta t) \\ \vdots \\ V_m(n_0-1,t-\Delta t) \\ V_m(n_0,t-\Delta t) \\ V_m(n_0+1,t-\Delta t) \\ \vdots \\ V_m(N,t-\Delta t) \end{bmatrix} + \frac{\Delta t}{C_m} \begin{bmatrix} I_{in}(1,t) \\ \vdots \\ I_{in}(n_0-1,t) \\ I_{in}(n_0,t) \\ I_{in}(n_0+1,t) \\ \vdots \\ I_{in}(N,t) \end{bmatrix}$$

Using equation [4] with an appropriately selected (small-enough) time difference Δt (e.g., in the range of 0.05 μs-10 μs), the processor 80 may compute the sub-threshold transmembrane potential $V_m$ at each of the nodes under intracellular stimulation current $I_{in}$ for the electrical cable model (step 206). The transmembrane potential $V_m$ at the end of the stimulation pulse may be obtained at the end of the running time equal to the pulse width.

This finite difference method reduces the differential equation to linearly solvable equations, which significantly reduces the computation complexity. This method can also take advantage of matrix inverse functions that become available in many math libraries. If a matrix inverse function is not available, other linear algebra techniques, such as QR decomposition, can be employed to implement the pseudo-matrix inverse. The model solutions obtained using the finite difference method were able to reproduce the values of the passive step response per unit intracellular current obtained from the stimulation of a passive cable electrical network in PSPICE, as provided in Eduardo N. Warman, et al. To further reduce the computational intensity, one can also obtain an analytical fit to the solution of the passive cable model, i.e., sub-threshold transmembrane potential as a function of fiber node and time, i.e., $f(n,t)=V_m(n,t)$, such that the time-evolution process and matrix inversion are eliminated from the real-time computation. In this case, the specific transmembrane potential at node n and time t can be calculated from the explicit function f(n, t). As another example, a look-up table containing pulse width values and nodes can be generated, and then later accessed in real-time.

After the processor 80 estimates the transmembrane potentials at the nodes of the electrical cable model at the end of the intracellular stimulation pulse, the processor 80 estimates the extracellular field potentials $V_e$, induced by the electrical energy theoretically conveyed by the specified electrode configuration at the specified pulse width, at the nodes along the electrical cable model (step 208). The processor 80 then computes a total equivalent driving function of the extracellular field potentials at the nodes of the electrical cable model in accordance with the following equation (step 210):

$$TDF(n,t) = \sum_{j=-K}^{K} \psi_j AF(n+j,t),$$ [5]

where $AF(n)=V_e(n-1)-2*V_e(n)+V_e(n+1)$, $\psi_j$ is a weight for each node j as a function of pulse width and nerve fiber properties, K is the furthest node from the node $n_0$ for which the TDF is being presently computed, making the average window size equal to 2K+1. Because there is an equivalence between stimulation induced by extracellular field potentials $V_e$ and that by the intracellular current $I_{int}$, and the transmembrane voltage potential at a particular node can be induced by a set of intracellular currents at the node and its adjacent nodes, the total equivalent driving function provides an estimate of the transmembrane voltage potential at a particular node.

Notably, the weight $\psi_j$ represents the contribution of a stimulation (extracellular or intracellular) at j nodes away from the specific node, the nodal transmembrane potentials $V_m$ computed in accordance with equation [4] above can be respectively used as the weights $\psi_j$ at the nodes. Thus, the transmembrane potentials of the nodes $n_0$, $n_0\pm 1$, $n_0\pm 2$, ... $n_0\pm K$ along the electrical cable model at the end of the intracellular stimulation pulse (i.e., $V_m(n_0+j, t=PW, j=0, \pm 1, \pm 2, \ldots, \pm K)$ are used as the weights $\psi_j$.

After the TDF is computed for each of the nodes, the processor 80 performs a higher-level human-discernible function (step 212), such as determining the specific amplitude of the electrical energy based on the computed TDF, and instructing the IPG 14 to deliver electrical energy at the specific amplitude via the selected electrode configuration to stimulate the patient, or computing a volume of tissue activation based on the computed total equivalent driving function, and generating display signals for display of the volume of tissue activation on a monitor 76.

It should be appreciated that the foregoing finite difference method can be applied to more efficiently solve differential equations related to models of axons, such as electrical cable models, it can be applied to more efficiently solve differential equations related to models of other parts of neurons, such as Hodgkin-Huxley models of a cell body and dentrites.

Although the foregoing techniques have been described as being implemented in the CP 18, it should be noted that this technique may be alternatively or additionally implemented in the RC 16, and the processing functions of the technique can even be performed in the IPG 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system for use in providing therapy to a patient, comprising:
    a user input device configured for receiving input from a user; and
    processing circuitry configured for selecting an electrode configuration in response to receiving the input from the user, providing an electrical model of a neuronal element of the patient, providing a discrete approximation of a differential equation of a neural response parameter of the electrical model as a function of discrete space and as a function of a finite time difference, computing the neural response parameter in the differential equation approximation at a specified time for each of a plurality of points on a membrane of the neuronal element, and performing a human-discernible function based on the computed neural response parameters.

2. The neurostimulation system of claim 1, wherein the discrete approximation of the differential equation of the neural response parameter of the electrical model is a function of nodes along the electrical model, and the neural response parameter of the differential equation approximation is computed for each of the nodes.

3. The neurostimulation system of claim 1, wherein the neural response parameter is a transmembrane voltage potential.

4. The neurostimulation system of claim 1, wherein the neuronal element is a neural axon.

5. The neurostimulation system of claim 2, wherein the electrical model is an electrical cable model of the neural axon, and the processing circuitry is further configured for estimating extracellular field potentials, induced by pulsed electrical energy theoretically conveyed by the electrode configuration, at the nodes along the electrical cable model, and computing a total equivalent driving function of the extracellular field potentials at at least one of the nodes, wherein each of the total equivalent driving functions comprises a plurality of activating functions that are respectively weighted using the computed neural response parameters, and the human-discernible function is performed based on the total equivalent driving function.

6. The neurostimulation system of claim 5, wherein the processing circuitry is configured for selecting a pulse width of the electrical energy in response to the input from the user, and computing the neural response parameters at the end of the pulse width.

7. The neurostimulation system of claim 5, wherein the differential equation approximation has a unit intracellular step current.

8. The neurostimulation system of claim 1, wherein the finite time difference is one of a forward time difference, a backward time difference, and a central time difference.

9. The neurostimulation system of claim 1, wherein the finite time difference is in the range of 0.05 µs-10 µs.

10. The neurostimulation system of claim 1, wherein the human-discernible function is instructing a neurostimulation device to deliver electrical energy to the patient at a specified amplitude.

11. The neurostimulation system of claim 10, further comprising output circuitry, wherein the processing circuitry is configured for instructing the neurostimulation device to deliver the electrical energy via the output circuitry.

12. The neurostimulation system of claim 1, wherein the human-discernible function is instructing a monitor to display a volume of tissue activation.

13. The neurostimulation system of claim 12, further comprising the monitor.

14. The neurostimulation system of claim 1, further comprising a housing containing the user input device and the processing circuitry.

15. The neurostimulation system of claim 14, further comprising an external control device comprising the housing, user input device, and the processing circuitry.

* * * * *